United States Patent [19]

Paget et al.

[11] 4,153,709

[45] May 8, 1979

[54] N-HETEROCYCLIC UREAS AS IMMUNE REGULANTS

[75] Inventors: Charles J. Paget, Indianapolis; John L. Sands, West Lafayette, both of Ind.

[73] Assignee: Eli Lilly and Company, Indianapolis, Ind.

[21] Appl. No.: 843,775

[22] Filed: Oct. 20, 1977

Related U.S. Application Data

[60] Division of Ser. No. 651,322, Jan. 21, 1976, Pat. No. 4,088,760, which is a continuation-in-part of Ser. No. 574,997, May 6, 1975, abandoned, which is a division of Ser. No. 398,607, Sep. 19, 1973, abandoned, which is a continuation-in-part of Ser. No. 185,823, Oct. 1, 1971, abandoned, which is a continuation-in-part of Ser. No. 794,756, Jan. 28, 1969, abandoned.

[51] Int. Cl.$^2$ .................. A61K 31/415; C07D 235/04

[52] U.S. Cl. ....................... 424/273 B; 424/270; 424/272; 548/326; 548/329

[58] Field of Search ................ 424/273 B; 548/326, 548/329

[56] References Cited

U.S. PATENT DOCUMENTS

| 3,399,212 | 8/1968 | Hoover et al. | 260/309.2 |
| 4,088,768 | 5/1978 | Paget et al. | 424/270 |

Primary Examiner—Leonard Schenkman
Attorney, Agent, or Firm—James L. Rowe; Everet F. Smith

[57] ABSTRACT

Benzimidazolyl, benzothiazolyl and benzoxazolyl ureas and thioureas are employed as immune regulatory agents, as agents capable of altering the immune response in mammals.

3 Claims, No Drawings

N-HETEROCYCLIC UREAS AS IMMUNE REGULANTS

This application is a division of application Ser. No. 651,322, filed Jan. 21, 1976, now U.S. Pat. No. 4,088,760 issued May 9, 1978, which was a continuation-in-part of our copending application Ser. No. 574,997, filed May 6, 1975, now abandoned, which was a division of our then copending Ser. No. 398,607, filed Sept. 19, 1973, now abandoned, which was a continuation-in-part of our then copending application Ser. No. 185,823, filed Oct. 1, 1971, now abandoned, which was a continatuion-in-part of our then copending application Ser. No. 794,756, filed Jan. 28, 1969, now abandoned.

BACKGROUND OF THE INVENTION 2-substituted benzimidazoles, benzothiazoles and benzoxazoles have recently been proposed for a variety of uses, mainly in the agricultural field. For example, 2-trifluoromethylbenzimidazoles are reported to be extremely active herbicides according to Great Britain Pat. No. 1,087,561. The compounds therein disclosed are also reported to have molluscidal, insecticidal and fungicidal properties. Other 2-substituted benzimidazoles have been found to be active coccidiostats. In particular, 2-(4-thiazolyl) benzimidazole (thiabendazole) is presently being marketed as an anthelmintic. In addition, certain 2-hydroxybenzylbenzimidazoles have been revealed as having anti-viral properties (see U.S. Pat. No. 3,331,739). While the use of benzoxazoles and benzothiazoles in the above areas has not been quite as thoroughly explored as that of benzimidazoles, there is, nevertheless, considerable interest in compounds of this structure, particularly as coccidiostats.

Urea derivatives of the above classes of compounds are sparingly described in the art. N-(2-benzothiazolyl)-N'-phenyl urea is described in *Chem. Abs.* 29, 2660; 55, 8389; 57, 801; the corresponding 4-methyl compound is described in *Chem. Abs.* 25, 104; 50, 1776–1777; and the corresponding 5-methoxy derivative is described in *Chem. Abs.* 52, 20673. N-(2-benzimidazolyl)-N'-phenyl urea is described in *Beilstein* 24, (II) 62 and in *Chem. Abs.* 15, 3077. In addition U.S. Pat. No. 3,299,085 discloses N-(2-benzothiazolyl) or N-(2-benzoxazolyl)-N'-$C_1$-$C_5$ aliphatic ureas as intermediates in the preparation of certain herbicides, and U.S. Pat. No. 3,162,644 describes 2-benzoxazolyl ureas, useful as plant growth regulators and muscle relaxants. U.S. Pat. Nos. 3,399,212; 3,336,191; and 3,401,171 disclose benzimidazolyl ureas said to be anthelmintics. Finally, South African Pat. No. 68/4748 (Derwent Pharmdoc basic, number 36565) discloses benzothiazolyl ureas as antiseptics in detergent compositions.

Recently, immune suppressant agents have come into prominence because of their use during transplants of organs from one human to another, and in particular in connection with organ transplant operations such as heart transplants, and in particular kidney transplants. It is part of the defense mechanism of humans to remove foreign antigens (in this case, the transplanted organ) by the immune reaction. Thus, in all of the organ transplant operations, it has been necessary to give large doses of an immune suppressant prior to the operation and continuing thereafter in order to prevent the host from rejecting the donor organ. The immune suppressant of choice is azathioprine (U.S. Pat. No. 3,056,785)

The immune response is composed of a sequence of cellular transformations and biochemical events leading to a bimodal response to foreign substances (antigens). Cells which are to participate in the response evolve from stem cells which originate in the bone marrow and are seeded out to the peripheral lymphoid organs. From these latter sites, following antigenic stimulus, the body's response is mounted in the form of plasma cells (which produce antibody) and specific immune lymphocytes. Antibody is released into the circulatory system and thus may act at a distance from the producing cell (humoral immunity). Specific immune lymphocytes also enter the circulatory system and act at the site of injury (cellular immunity). The reaction of antibody with antigen triggers the release of histamine from basophilic leucocytes; histamine, in turn, alters the permeability of blood vessels, speeding the influx of both antibody and specific immune lymphocytes into the sites of injury. Thus, the immune response is composed of a series of biochemical events in a sequence of cells at various sites in the body. It can be altered—suppressed, in the case of the compounds herein discussed—at a number of biochemical or cellular developmental sites.

Antihistamines only affect a secondary reaction in the immune response, having no direct effect on antibody-producing cells or specific immune lymphocytes. A number of agents, currently in use as immuno-suppressive drugs, act further back in the chain of events called herein the immune response. Certain antiinflammatory steroids, e.g., cortisone, suppress production of antibody and specific immune lymphocytes, but also radically deplete normal lymphoid tissue and have other undesirable side effects. Certain antineoplastic drugs, e.g., azathioprine, cyclophosphamide, and methotrexate, are employed as immunosuppressives, but they also deplete normal lymphoid tissue and radically depress other bone-marrow-derived cells. The general cytotoxicity of the latter drugs is to be expected in view of their having been selected on the basis of toxicity against a spectrum of cell types.

It is an object of this invention to provide a method of altering the immune response through the use of agents selected on the basis of specificity of action against cells functioning in the immune response.

DESCRIPTION OF THE INVENTION

In fulfillment of the above and other objects, this invention provides a method for altering the immune response in mammals comprising administering to said mammals an effective nontoxic dose within the range 0.1 to 500 mg/kg of mammalian body weight of at least one compound of the formula:

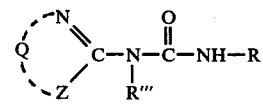

wherein
R is α-naphthyl, phenyl or substituted phenyl wherein said substituents can be one or more numbers of the group consisting of halo, $C_1$-$C_3$ alkoxy, $C_1$-$C_3$ alkyl or $CF_3$;
R''' is H or $CH_3$;
Y is S or O;
Z is S, O or NR'' wherein R'' is H, $CH_3$ or phenyl; and
Q is

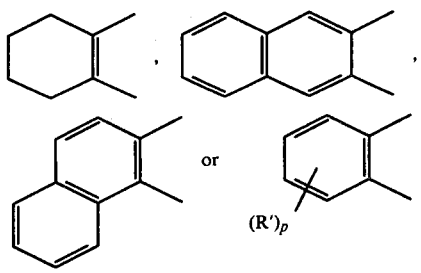

wherein
R' in each of its "p" occurrences independently represents halo, $CF_3$, carb-$C_1$-$C_3$-alkoxy, nitro, $C_1$-$C_3$ alkyl or $C_1$-$C_3$ alkoxy; and p is 0-2.

In the above formula, the term $C_1$-$C_3$ alkyl includes the radicals methyl, ethyl, isopropyl or n-propyl. When R is substituted phenyl, the substituent can be halo, such as fluorine, chlorine or bromine; $C_1$-$C_3$ alkoxy, such as methoxy, ethoxy, isopropoxy or n-propoxy; $C_1$-$C_3$ alkyl, the scope of which grouping is illustrated above or $CF_3$.

When R' is halo, $C_1$-$C_3$ alkyl or $C_1$-$C_3$ alkoxy, their scope is the same as that defined above for R. When R' is carb-$C_1$-$C_3$-alkoxy, groups which it represents include carbomethoxy, carboethoxy, carbo-n-propoxy and carboisopropoxy.

A preferred group of orally active immune alterant compounds useful in the process of this invention are represented by the formulas:

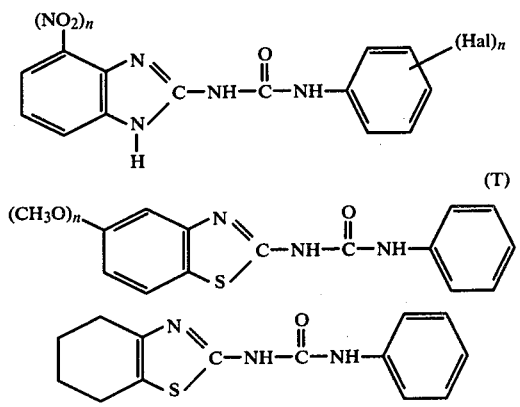

wherein
Hal is a halogen having an atomic number below about 82,

T is Hal or methyl, and n is 0 or 1.

Compounds represented by the above formulas which are useful in the therapeutic processes of this invention are prepared by reacting a 2-aminobenzimidazole, 2-aminobenzothiazole, or 2-aminobenzoxazole with an appropriately substituted isocyanate, thioisocyanate, thiocarbamoyl chloride or carbamoyl chloride according to the following reactions:

Reaction Scheme I

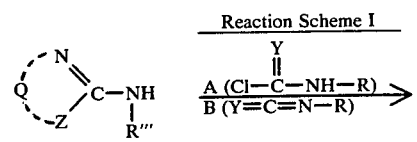

-continued
Reaction Scheme I

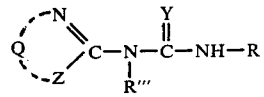

wherein Q, Z, Y, R, R' and R''' have the same meaning as hereinabove.

A typical preparation of a benzimidazolyl urea in which R' is hydrogen follows:

EXAMPLE 1

N-(2-Benzimidazolyl)-N'-naphthylurea

A solution was prepared containing 5.32 g. of 2-aminobenzimidazole in 150 ml. of tetrahydrofuran (THF). A second solution containing 6.76 g. of naphthyl isocyanate in 100 ml. of THF was added with stirring over a 30 minute period. The reaction mixture was heated at refluxing temperature for 6 hours and then cooled N-(2-benzimidazolyl)-N'-naphthylurea precipitated and was separated by filtration. Recrystallization of the filter cake from acetone yielded purified N-(2-benzimidazolyl)-N'-naphthylurea melting at 327°-328° C.

Tables 1-15 which follow contain analytical data and melting points for illustrative compounds coming within the scope of this invention prepared as indicated above.

Starting materials useful in the above process are either available from commercial sources or are prepared by reacting the appropriately substituted o-phenylene diamine with cyanogen bromide according to the method of Leonard et al., *J. Am. Chem. Soc.* 69, 2459 (1947).

Starting materials prepared by the above procedure include the following:

2-amino-5(6)-chlorobenzimidazole
   M.P.=158°-161° C.

2-amino-5(6)-trifluoromethylbenzimidazole
   M.P.=152°-155° C.

2-amino-5(6)-methylbenzimidazole
   M.P.=192°-199° C.

In the reaction scheme I above, when a 2-aminobenzimidazole is used as one of the reactants, the first step of the reaction is the formation of a 1-carboxanilide or carboamide, which rearranges upon heating to the desired 2-benzimidazolyl urea. This reaction is illustrated in reaction scheme II below, in which PH is phenyl or substituted phenyl, wherein said substituents are one or more members of the group consisting of halo, $C_1$-$C_3$ alkoxy, $C_1$-$C_3$ alkyl, or $CF_3$. The scope of the phenyl substituents has been fully illustrated above in illustrating the scope of the term R, substituted phenyl being one of the permissible groupings for R.

Reaction Scheme II

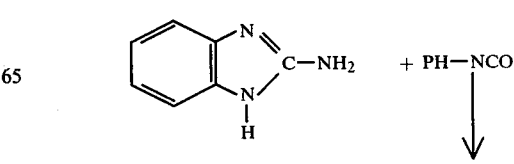

-continued
Reaction Scheme II

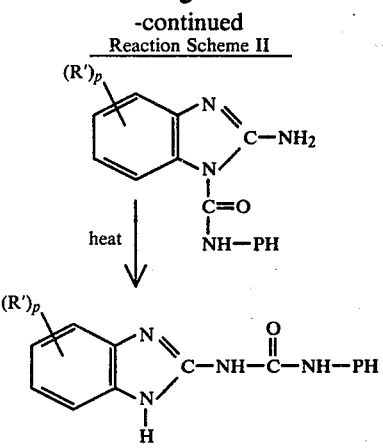

The 1-substituted derivatives can be isolated when the reaction is carried out below 15° C. and preferably at about 0° C. The rearrangement of the 1-substituted compound to the benzimidazolyl urea itself is readily accomplished by heating the 1-substituted derivative to about 50° C. The same type of intermediate formation of a 2-amino-4-benzimidazolyl carboxanilide or carboxamide followed by rearrangement to a 2-benzimidazolyl urea occurs when a carbamoyl chloride is reacted with a 2-aminobenzimidazole as illustrated in route B, reaction scheme I above.

Compounds in which R''' is methyl are prepared by alkylation of the corresponding compound in which R''' is hydrogen.

As previously stated, the compositions of this invention are employed in altering the immune reaction in mammals. Thus, the compounds can be classed as "immune regulating agents" by which is meant an agent which can decrease the formation of antibodies to foreign protein. This activity can thus also be characterized as anti-allergic in that the allergic reaction is part of the defense mechanism of the body (the immune mechanism) against foreign antigens. (This activity is quite different from an antihistamine activity which affects only the effects of histamine released by an antibody-antigen reaction). Although immune regulating activity was determined in mice using sheep erythrocytes as the antigen, it should be understood that the same type of activity would be shown against any foreign protein (antigen) in any mammal.

The ability of compounds according to the above formulas to alter immune mechanisms in a host animal was measured by their activity according to the following test. Groups of five 20-gram Swiss mice were injected intraperitoneally with standardized suspensions of an antigen—in this instance sheep blook cells. The active compounds were also injected by the intraperitoneal route at various times before and/or after the injection of the red blood cells. Eight days after injection of the antigen, the mice were bled and the sera from each group pooled. Antibody determinations were made on the serum pools by a hemaglutination pattern procedure and comparisons made between treated and control animals. In Tables 1–18 which follow, the activity of the compounds listed therein is given in terms of the minimum dose of drug necessary to suppress the hemaglutination titer by a 4-fold factor in the treated mice as compared with control titers.

In Tables 1–15, a blank space indicates that the compound listed has not yet been tested as an immune regulating agent in mammals, and a dash indicates that the compound was not active at the highest dose tested, usually 100 mg./kg. in the immune regulating test, but presumably would be active at higher dose levels.

TABLE 1

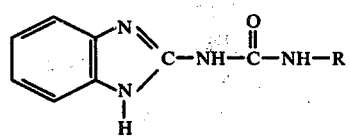

| R | R' | Melting Point °C. | Analysis Calculated C | H | N | Analysis Found C | H | N | Immuno-Suppressant ED4-Fold mg./kg. × 3 |
|---|---|---|---|---|---|---|---|---|---|
| phenyl | H | 329–30 | 66.65 | 4.79 | 22.21 | 66.36 | 4.96 | 21.95 | 12.5 |
| α-naphthyl | H | 327–8 | 71.51 | 4.67 | 18.53 | 71.55 | 3.53 | 18.13 | 3.1 |
| p-chlorophenyl | H | 349–51 | 58.64 | 3.86 | 19.54 | 58.93 | 4.06 | 19.37 | 12.5 |
| m-chlorophenyl | H | 344–5 | 58.64 | 3.86 | 19.54 | 58.72 | 3.74 | 19.29 | 3.1 |
| o-chlorophenyl | H | 331–3 | 58.64 | 3.86 | 19.54 | 58.68 | 3.65 | 19.30 | 12.5 |
| p-fluorophenyl | H | 338–9 | 62.21 | 4.10 | 20.73 | 62.00 | 4.26 | 20.68 | 6.2 |
| o-fluorophenyl | H | 347–8 | 62.21 | 4.10 | 20.73 | 62.41 | 4.30 | 20.67 | 1.6 |
| m-trifluoromethylphenyl | H | 336–7 | 56.24 | 3.46 | 17.49 | 56.45 | 3.67 | 17.44 | 100 |
| p-tolyl | H | 342–3 | 67.65 | 5.30 | 21.04 | 67.64 | 5.54 | 20.84 | 6.2 |
| o-tolyl | H | 339–340 | 67.65 | 5.30 | 21.04 | 67.87 | 5.57 | 20.92 | 25 |
| p-bromophenyl | H | 342–3 | 50.77 | 3.35 | 16.92 | 51.03 | 3.51 | 16.83 | 100 |
| 3,4-dichlorophenyl | H | 337–8 | 52.35 | 3.13 | 17.44 | 52.64 | 3.32 | 17.64 | 0.8 |

TABLE 2

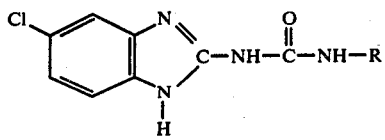

| R | Melting Point °C. | Analysis Calculated C | H | N | Analysis Found C | H | N | Immuno-Suppressant ED4-Fold mg./kg. × 3 |
|---|---|---|---|---|---|---|---|---|
| phenyl | 339–40 | 58.65 | 3.87 | 19.54 | 58.65 | 4.02 | 19.64 | 25 |
| α-naphthyl | 342–3 | 64.19 | 3.89 | 1664 | 63.97 | 4.13 | 16.88 | 6.2 |
| p-chlorophenyl | 329–30 | 52.36 | 3.14 | 17.45 | 52.24 | 3.40 | 17.07 | 6.2 |
| o-chlorophenyl | 340 | 52.36 | 3.14 | 17.45 | 51.99 | 3.12 | 17.05 | 100 |
| p-fluorophenyl | 348–50 | 55.18 | 3.30 | 18.38 | 55.03 | 3.27 | 18.45 | <12.5 |
| o-fluorophenyl | 339–40 | 55.18 | 3.30 | 18.38 | 55.45 | 3.56 | 18.38 | <100 |
| p-tolyl | 319–20 | 59.90 | 4.35 | 19.04 | 59.85 | 4.62 | 18.90 | 50 |
| o-tolyl | 307–8 | 59.90 | 4.35 | 18.63 | 59.81 | 4.63 | 18.48 | 100 |
| m-tolyl | 315–16 | 59.90 | 4.35 | 18.63 | 59.88 | 4.15 | 18.36 | 25 |
| o-anisyl | 340–2 | 56.87 | 4.13 | 17.68 | 56.69 | 4.09 | 17.48 | <6.2 |

TABLE 3

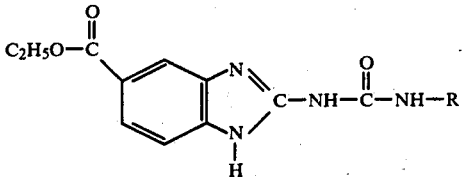

| R | Melting Point °C. | Analysis Calculated C | H | N | Analysis Found C | H | N | Immuno-Suppressant ED4-Fold mg./kg. × 3 |
|---|---|---|---|---|---|---|---|---|
| phenyl | 327–8 | 62.95 | 4.97 | 17.28 | 63.12 | 4.99 | 17.49 | <25 |
| α-naphthyl | 315–6 | 67.37 | 4.85 | 14.97 | 67.28 | 4.94 | 14.94 | 6.2 |
| p-chlorophenyl | 309–11 | 56.90 | 4.21 | 15.62 | 56.61 | 4.30 | 15.82 | 50 |
| m-chlorophenyl | 308–310 | 56.90 | 4.21 | 15.62 | 56.85 | 4.50 | 15.67 | 50 |
| o-chlorophenyl | 308–9 | 56.90 | 4.21 | 15.62 | 56.69 | 5.79 | 15.32 | 0.4 |
| p-fluorophenyl | 310–11 | 59.64 | 4.41 | 16.36 | 59.92 | 4.62 | 16.33 | 25 |
| o-fluorophenyl | 315–16 | 59.64 | 4.41 | 16.36 | 59.75 | 4.67 | 16.65 | <6.2 |
| m-trifluoromethylphenyl | 328–9 | 55.1 | 3.85 | 14.28 | 54.82 | 4.02 | 14.37 | 100 |
| p-tolyl | 305–7 | 63.89 | 5.36 | 16.56 | 63.71 | 5.39 | 16.30 | 100 |
| m-tolyl | 321–3 | 63.89 | 5.36 | 16.56 | 63.91 | 6.58 | 16.51 | <12.5 |
| o-tolyl | 304–5 | 63.89 | 5.36 | 16.56 | 64.03 | 5.39 | 16.74 | 25 |

TABLE 4

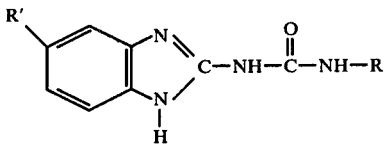

| R | R' | Melting Point °C. | Analysis Calculated C | H | N | Analysis Found C | H | N | Immuno-Suppressant ED4-Fold mg./kg. × 3 |
|---|---|---|---|---|---|---|---|---|---|
| phenyl | CF$_3$ | 309–310 | 56.25 | 3.46 | 17.49 | 56.44 | 3.46 | 17.78 | 12.5 |
| α-naphthyl | CF$_3$ | 307–8 | 61.61 | 3.53 | 15.13 | 61.89 | 3.78 | 14.99 | <50 |
| am-chlorophenyl | CF$_3$ | 320–2 | 50.78 | 2.84 | 15.79 | 51.01 | 2.97 | 15.84 | 50–200 |
| phenyl | CH$_3$ | 327–8 | 67.64 | 5.30 | 21.04 | 67.41 | 5.42 | 20.85 | 100 |
| α-naphthyl | CH$_3$ | 315–6 | 72.13 | 5.10 | 17.71 | 71.96 | 5.25 | 17.62 | <0.4 |

TABLE 5

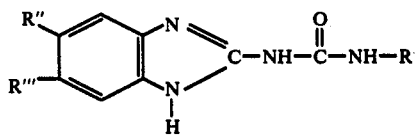

| R | R'' | R''' | Melting Point °C. | Analysis Calculated C | H | N | Analysis Found C | H | N | Immuno-Suppressant ED4-Fold mg./kg. × 3 |
|---|---|---|---|---|---|---|---|---|---|---|
| phenyl | $CH_3$ | $CH_3$ | 336–7 | 68.55 | 5.75 | 19.99 | 68.62 | 5.72 | 19.81 | 12.5 |
| α-naphthyl | $CH_3$ | $CH_3$ | 298–300 | 71.70 | 5.40 | 16.76 | 71.43 | 5.04 | 16.42 | 50 |
| p-chlorophenyl | $CH_3$ | $CH_3$ | 351–2 | 61.04 | 4.80 | 17.80 | 61.07 | 4.78 | 17.77 | 12.5 |
| m-chlorophenyl | $CH_3$ | $CH_3$ | 342–3 | 61.04 | 4.80 | 17.80 | 60.99 | 5.08 | 17.99 | 800 |
| 3,4-dichlorophenyl | $CH_3$ | $CH_3$ | 343–5 | 55.02 | 4.04 | 16.04 | 54.91 | 4.20 | 15.99 | 100 |
| 2,5-dichlorophenyl | $CH_3$ | $CH_3$ | 336–7 | 55.02 | 4.04 | 16.04 | 54.81 | 4.19 | 16.19 | <25 |
| 2,4-difluorophenyl | $CH_3$ | $CH_3$ | 327–8 | 64.41 | 5.06 | 18.78 | 64.22 | 5.10 | 18.92 | 0.4 |
| o-fluorophenyl | $CH_3$ | $CH_3$ | 321–2 | 64.41 | 5.06 | 18.78 | 64.52 | 5.33 | 18.79 | 100 |
| p-tolyl | $CH_3$ | $CH_3$ | 344–5 | 69.37 | 6.16 | 19.04 | 69.24 | 6.10 | 19.26 | 3.0 |
| m-tolyl | $CH_3$ | $CH_3$ | 329–30 | 69.37 | 6.16 | 19.04 | 69.19 | 6.25 | 19.01 | 12.5 |
| o-tolyl | $CH_3$ | $CH_3$ | 342–5 | 69.37 | 6.16 | 19.04 | 69.47 | 6.30 | 19.28 | 12.5 |
| p-bromophenyl | $CH_3$ | $CH_3$ | 335–6 | 53.49 | 4.20 | 15.59 | 53.81 | 4.42 | 15.23 | 12.5 |
| p-anisyl | $CH_3$ | $CH_3$ | 343–5 | 65.79 | 5.85 | 18.05 | 65.51 | 6.06 | 18.28 | 12.5 |
| phenyl | Cl | Cl | 364–5 | 52.35 | 3.13 | 17.44 | 52.10 | 3.29 | 17.54 | 12.5 |
| α-naphthyl | Cl | Cl | 339–40 | 58.23 | 3.25 | 15.09 | 58.30 | 3.50 | 15.20 | >12.5 |

TABLE 6

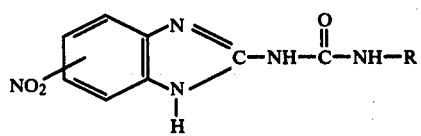

| Position of $NO_2$ | R | Melting Point °C. | Analysis Calculated C | H | N | Analysis Found C | H | N | Immuno-Suppressant ED4-Fold mg./kg. × 3 |
|---|---|---|---|---|---|---|---|---|---|
| 4(7) | phenyl | 361–2 | 56.56 | 3.73 | 23.56 | 56.78 | 3.84 | 23.82 | 25 |
| 4(7) | o-fluorophenyl | 355–6 | 53.33 | 3.20 | 22.22 | 53.38 | 3.33 | 22.11 | 3.1 |

TABLE 7

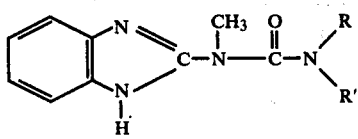

| R | R' | Melting Point °C. | Analysis Calculated C | H | N | Analysis Found C | H | N | Immuno-Suppressant ED4-Fold mg./kg. × 3 |
|---|---|---|---|---|---|---|---|---|---|
| phenyl | H | 189–190 | 67.65 | 5.30 | 21.04 | 67.52 | 5.39 | 21.02 | 50 |
| m-chlorophenyl | H | 158–9 | 59.90 | 4.36 | 18.63 | 59.98 | 4.44 | 18.67 | 25 |
| α-naphthyl | H | 205–6 | 72.13 | 5.10 | 17.71 | 72.41 | 5.25 | 17.63 | 25 |
| p-chlorophenyl | H | 195–6 | 59.90 | 4.36 | 18.63 | 59.86 | 4.62 | 18.35 | 50 |

TABLE 8

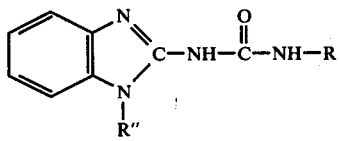

| R | R'' | Melting Point °C. | Analysis Calculated C | H | N | Analysis Found C | H | N | Immuno-Suppressant ED4-Fold mg./kg. × 3 |
|---|---|---|---|---|---|---|---|---|---|
| phenyl | phenyl | 170–1 | 73.15 | 4.91 | 17.06 | 73.19 | 5.11 | 17.35 | 50 |
| α-naphthyl | phenyl | 166–7 | 76.17 | 4.79 | 14.81 | 75.97 | 4.82 | 14.75 | 100 |
| phenyl | methyl | 181–2 | 67.65 | 5.30 | 21.04 | 67.92 | 5.58 | 21.20 | 3.1 |
| α-naphthyl | methyl | 238–9 | 72.13 | 5.10 | 17.71 | 71.88 | 5.04 | 17.73 | >50 |
| m-chlorophenyl | methyl | 190–1 | 59.90 | 4.36 | 18.63 | 60.13 | 4.31 | 18.75 | 6.2 |

TABLE 8-continued

| R | R″ | Melting Point °C. | Analysis Calculated C | H | N | Analysis Found C | H | N | Immuno-Suppressant ED4-Fold mg./kg. × 3 |
|---|---|---|---|---|---|---|---|---|---|
| p-chlorophenyl | methyl | 199–200 | 59.90 | 4.36 | 18.63 | 59.91 | 4.38 | 18.86 | >50 |

TABLE 9

| R | Melting Point °C. | Analysis Calculated C | H | N | Analysis Found C | H | N | Immuno-Suppressant ED4-Fold mg./kg. × 3 |
|---|---|---|---|---|---|---|---|---|
| phenyl | 362–4 | 71.51 | 4.67 | 18.53 | 71.54 | 4.93 | 18.79 | 25 |
| α-naphthyl | 330 | 74.98 | 4.58 | 15.90 | 4.77 | 4.80 | 15.61 | 50 |
| p-fluorophenyl | 364–5 | 67.48 | 4.09 | 17.49 | 67.62 | 4.38 | 17.28 | >25 |

TABLE 10

| R | Melting Point °C. | Analysis Calculated C | H | N | Analysis Found C | H | N | Immuno-Suppressant ED4-Fold mg./kg. × 3 |
|---|---|---|---|---|---|---|---|---|
| phenyl | 348–9 | 71.51 | 4.67 | 18.53 | 71.75 | 4.87 | 18.29 | 50 |
| α-naphthyl | 331–2 | 74.98 | 4.58 | 15.90 | 75.09 | 4.78 | 15.98 | >6.2 |
| m-chlorophenyl | 354–5 | 64.18 | 3.88 | 16.62 | 64.19 | 3.91 | 16.41 | .05 |
| p-fluorophenyl | 349–50 | 67.49 | 4.09 | 17.49 | 67.27 | 4.28 | 17.72 | 25 |

TABLE 11

| R | R′ | Y | Melting Point °C. | Analysis Calculated C | H | N | Analysis Found C | H | N | Immuno-Suppressant ED4-Fold mg./kg. × 3 |
|---|---|---|---|---|---|---|---|---|---|---|
| phenyl | H | S | 333–5 | 62.44 | 4.12 | 15.61 | 62.23 | 4.33 | 15.82 | 6.2 |
| α-naphthyl | H | S | 278–280 | 67.70 | 4.11 | 13.16 | 67.97 | 4.21 | 13.31 | <50 |
| p-chlorophenyl | H | S | 315–16 | 55.35 | 3.32 | 13.83 | 55.47 | 3.60 | 13.59 | <6.2 |
| m-chlorophenyl | H | S | 329–30 | 55.35 | 3.32 | 13.83 | 55.61 | 3.57 | 13.79 | 1.6 |
| o-chlorophenyl | H | S | 335–6 | 55.35 | 3.32 | 13.83 | 55.17 | 3.42 | 14.03 | <50 |
| 3,4-dichlorophenyl | H | S | 316–7 | 49.71 | 2.68 | 12.42 | 49.85 | 2.77 | 12.19 | 12.5 |
| p-fluorophenyl | H | S | 341–2 | 58.52 | 3.51 | 14.63 | 58.33 | 3.62 | 14.67 | <25 |
| o-fluorophenyl | H | S | 333–333.5 | 58.52 | 3.51 | 14.63 | 58.74 | 3.67 | 14.93 | <6.2 |
| 2,5-dichlorophenyl | H | S | 327–8 | 49.71 | 2.68 | 12.42 | 49.83 | 2.55 | 12.56 | 12.5 |
| α-naphthyl | 4-Cl | S | 256–8 | 59.73 | 3.53 | 12.29 | 59.94 | 3.30 | 12.04 | <12.5 |
| m-chlorophenyl | 4-Cl | S | 266–8 | 49.71 | 2.68 | 12.42 | 49.60 | 2.96 | 12.19 | <50 |
| phenyl | H | O | 192–3 | 66.39 | 4.38 | 16.59 | 66.31 | 4.63 | 16.89 | 50 |
| α-naphthyl | H | O | 232–5 | 71.27 | 4.32 | 13.86 | 71.00 | 4.59 | 13.65 | 50 |
| phenyl | 5-Cl | O | 202–3 | 58.44 | 3.50 | 14.61 | 58.59 | 3.68 | 14.53 | 200 |
| α-naphthyl | 5-Cl | O | 234–5 | 64.00 | 3.58 | 12.44 | 63.97 | 3.78 | 12.37 | 200 |
| m-chlorophenyl | 5-Cl | O | 233–5 | 52.19 | 2.81 | 13.04 | 52.10 | 2.94 | 12.79 | 400 |
| m-trifluoromethyl-phenyl | H | S | 328–9 | 53.41 | 2.99 | 12.46 | 53.61 | 3.22 | 12.29 | <50 |

TABLE 11-continued

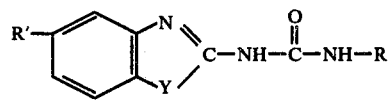

| R | R' | Y | Melting Point °C. | Analysis Calculated C | H | N | Analysis Found C | H | N | Immuno-Suppressant ED4-Fold mg./kg. × 3 |
|---|---|---|---|---|---|---|---|---|---|---|
| o-tolyl | H | S | 335-6 | 63.59 | 4.63 | 14.83 | 63.86 | 4.54 | 14.80 | <50 |
| p-tolyl | H | S | 327-8 | 63.59 | 4.63 | 14.83 | 63.80 | 4.72 | 14.73 | 100 |
| p-bromophenyl | H | S | 298-300 | 48.28 | 2.89 | 12.06 | 48.18 | 2.92 | 12.13 | 100 |
| p-anisyl | H | S | 325-6 | 60.19 | 4.38 | 14.04 | 60.03 | 4.44 | 13.83 | 50 |
| o-ethoxyphenyl | H | S | 336-7 | 61.32 | 4.82 | 13.40 | 61.05 | 4.70 | 13.50 | <50 |
| o-anisyl | H | S | 339-40 | 60.19 | 4.38 | 14.04 | 60.19 | 4.58 | 13.75 | 50 |
| phenyl | 4-Cl | S | 268-70 | 55.35 | 3.31 | 13.83 | 55.62 | 3.60 | 13.66 | <12.5 |
| phenyl | 5,6-dimethyl | S | 370-2 | 64.62 | 5.09 | 14.14 | 64.91 | 5.41 | 14.48 | 100 |
| α-naphthyl | 5,6-dimethyl | S | 355-6 | 69.15 | 4.93 | 12.10 | 69.18 | 5.18 | 12.05 | 50 |
| p-chlorophenyl | 5,6-dimethyl | S | 359-60 | 57.92 | 4.25 | 12.66 | 58.00 | 4.24 | 12.42 | 25 |
| m-chlorophenyl | 5,6-dimethyl | S | 345-6 | 57.92 | 4.25 | 12.66 | 58.42 | 4.46 | 13.06 | 100 |
| o-chlorophenyl | 5,6-dimethyl | S | 353-4 | 57.92 | 4.25 | 12.66 | 58.14 | 4.26 | 12.49 | <100 |
| 3,4-dichlorophenyl | 5,6-dimethyl | S | 331-2 | 52.46 | 3.58 | 11.47 | 52.76 | 3.74 | 11.56 | 50 |
| p-fluorophenyl | 5,6-dimethyl | S | 353-4 | 60.93 | 4.47 | 13.32 | 60.89 | 4.50 | 13.03 | 12.5 |
| o-fluorophenyl | 5,6-dimethyl | S | 355-6 | 60.93 | 4.47 | 13.32 | 60.69 | 4.73 | 13.22 | <1.6 |
| m-trifluorophenyl | 5,6-dimethyl | S | 348-9 | 55.88 | 3.86 | 11.50 | 56.01 | 4.00 | 11.28 | 25 |
| p-tolyl | 5,6-dimethyl | S | 349-50 | 65.58 | 5.50 | 13.50 | 65.35 | 5.42 | 13.51 | 100 |
| m-tolyl | 5,6-dimethyl | S | 349-50 | 65.58 | 5.50 | 13.50 | 65.62 | 5.65 | 13.39 | 25 |
| o-tolyl | 5,6-dimethyl | S | 340-1 | 65.58 | 5.50 | 13.50 | 65.60 | 5.65 | 13.27 | <25 |
| 2,5-dichlorophenyl | 5,6-dimethyl | S | 360-1 | 52.46 | 3.57 | 11.47 | 52.36 | 3.49 | 11.71 | <12.5 |
| p-bromophenyl | 5,6-dimethyl | S | 340-1 | 51.06 | 3.74 | 11.16 | 51.31 | 3.92 | 11.00 | 100 |
| phenyl | 6-CH$_3$O | S | 321-2 | 60.19 | 4.38 | 14.04 | 59.95 | 4.42 | 14.03 | <25 |
| α-naphthyl | 6-CH$_3$O | S | 297-8 | 65.32 | 4.33 | 12.03 | 65.21 | 4.56 | 12.26 | <50 |
| p-chlorophenyl | 6-CH$_3$O | S | 310-11 | 53.96 | 3.62 | 12.58 | 54.20 | 3.82 | 12.31 | <50 |
| m-chlorophenyl | 6-CH$_3$O | S | 306-7 | 53.96 | 3.62 | 12.58 | 54.06 | 4.06 | 12.50 | 12.5 |
| o-chlorophenyl | 6-CH$_3$O | S | 314-5 | 53.97 | 3.62 | 12.59 | 53.84 | 3.90 | 12.34 | <50 |
| o-fluorophenyl | 6-CH$_3$O | S | 313-4 | 56.76 | 3.81 | 13.24 | 56.87 | 4.01 | 13.06 | <3.1 |
| p-tolyl | 6-CH$_3$O | S | 297-8 | 61.33 | 4.83 | 13.41 | 61.24 | 5.04 | 13.14 | <100 |
| o-tolyl | 6-CH$_3$O | S | 309-10 | 61.33 | 4.83 | 13.41 | 60.81 | 4.87 | 13.79 | <50 |
| m-tolyl | 6-CH$_3$O | S | 311-2 | 61.33 | 4.83 | 13.41 | 61.45 | 4.99 | 13.49 | <25 |
| p-bromophenyl | 6-CH$_3$O | S | 295 | 47.62 | 3.19 | 11.10 | 47.34 | 3.21 | 11.02 | 100 |

TABLE 12

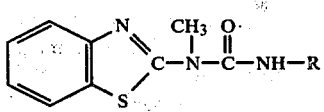

| R | Melting Point °C. | Analysis Calculated C | H | N | Analysis Found C | H | N | Immuno-Suppressant ED4-Fold mg./kg. × 3 |
|---|---|---|---|---|---|---|---|---|
| phenyl | 95 | 63.59 | 4.63 | 14.83 | 63.72 | 4.74 | 14.89 | 50 |
| α-naphthyl | 174-5 | 68.46 | 4.54 | 12.61 | 68.70 | 4.65 | 12.55 | 50 |
| p-chlorophenyl | 140-1 | 56.68 | 3.80 | 13.22 | 56.93 | 3.93 | 13.25 | <50 |

TABLE 13

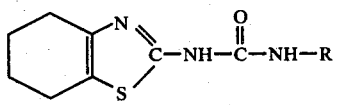

| R | Melting Point °C. | Analysis Calculated C | H | N | Analysis Found C | H | N | Immuno-Suppressant ED4-Fold mg./kg. × 3 |
|---|---|---|---|---|---|---|---|---|
| phenyl | 318-9 | | | 15.37 | | | 15.52 | 25 |
| α-naphthyl | 257-8 | 66.86 | 5.30 | 13.00 | 66.90 | 5.35 | 12.82 | <50 |

TABLE 14

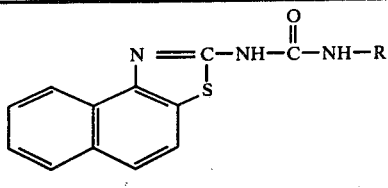

| R | Melting Point °C. | Analysis Calculated C | H | N | Analysis Found C | H | N | Immuno-Suppressant ED4-Fold mg./kg. × 3 |
|---|---|---|---|---|---|---|---|---|
| phenyl | 320–2 | 67.70 | 4.11 | 13.16 | 67.89 | 4.20 | 12.99 | <12.5 |
| α-naphthyl | 269–270 | 71.53 | 4.09 | 11.38 | 71.53 | 4.09 | 11.68 | 3.1 |
| p-chlorophenyl | 310–11 | 61.09 | 3.41 | 11.87 | 60.88 | 3.39 | 11.80 | <100 |
| m-chlorophenyl | 314–5 | 61.09 | 3.41 | 11.87 | 61.27 | 3.57 | 11.81 | <1.6 |
| o-chlorophenyl | 321–2 | 61.09 | 3.41 | 11.87 | 61.25 | 3.50 | 11.84 | 6.2 |
| 2,5-dichlorophenyl | 315–6 | 55.67 | 2.85 | 10.82 | 55.78 | 2.78 | 10.58 | 100 |
| p-fluorophenyl | 308–9 | 64.07 | 3.58 | 12.45 | 64.01 | 3.68 | 12.28 | 12.5 |
| o-fluorophenyl | 318–9 | 64.07 | 3.58 | 12.45 | 63.94 | 3.90 | 12.30 | 3.1 |
| 3,4-dichlorophenyl | 305–6 | 55.68 | 2.85 | 10.82 | 55.88 | 2.79 | 10.56 | 3.1 |
| m-trifluoromethyl-phenyl | 316–7 | 59.90 | 3.12 | 10.85 | 60.15 | 3.39 | 10.59 | <6.2 |
| p-tolyl | 307–8 | 68.46 | 4.54 | 12.61 | 68.53 | 4.82 | 12.33 | 6.2 |
| m-tolyl | 317–8 | 68.46 | 4.54 | 12.61 | 68.68 | 4.59 | 12.38 | 3.1 |
| o-tolyl | 319–20 | 68.46 | 4.54 | 12.61 | 68.52 | 4.69 | 12.32 | <1.6 |
| p-bromophenyl | 316–7 | 54.27 | 3.03 | 10.55 | 54.23 | 3.17 | 10.60 | <50 |

TABLE 15

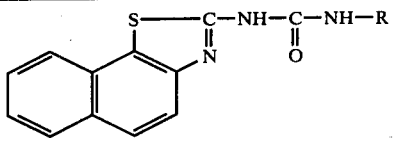

| R | Melting Point °C. | Analysis Calculated C | H | N | Analysis Found C | H | N | Immuno-Suppressant ED4-Fold mg./kg. × 3 |
|---|---|---|---|---|---|---|---|---|
| phenyl | 353–4 | 67.70 | 4.11 | 13.16 | 67.98 | 4.04 | 13.22 | 0.8 |
| α-naphthyl | 346–7 | 71.53 | 4.09 | 11.38 | 71.36 | 4.14 | 11.50 | 0.4 |
| p-tolyl | 369–70 | 68.46 | 4.54 | 12.61 | 68.21 | 4.59 | 12.76 | >25 |
| p-bromophenyl | 357–8 | 54.28 | 3.03 | 10.55 | 54.18 | 3.13 | 10.42 | 50 |

In addition to their use in organ transplant operations, immune regulating agents are also useful in various diseases of little-understood etiology, denominated generically as "auto-immune" diseases. These diseases include: auto-immune hemolytic anemia, idiopathic thrombocytopenic purpura, lupus erythematosus, lupoid hepatitis, lupus nephritis, glomerulonephritis, the nephrotic syndrome, Goodpasture's syndrome, Wegener's granulomatosis, scleroderma, Sezary's disease, psoriasis, uveitis, rheumatoid arthritis, ulcerative colitis, thyroiditis and mumps orchitis. Auto-immune suppressant agents, such as azathiaprene, generally may be more or less useful in the treatment of the above diseases depending upon the degree to which the disease is dependent upon an auto-immune mechanism.

Other routes of administration include oral, topical and subcutaneous routes. For oral administration, the immune suppressant can be dissolved or suspended in polyethylene glycol and mixed with corn oil, at a rate of 1–200 mg/ml. A particularly useful medium for oral administration contains 50 percent polyethylene glycol 200, 40 percent corn oil and 10 percent polyoxyethylene sorbitol monostearate. Aqueous vehicles, to which may be added surface-active agents, are also useful. For topical application, the compound is preferably administered in ethanol or in the above polyethylene glycol-corn oil-surfactant composition whereas for subcutaneous injection an isotonic solution is used. The immuneregulant is present in the particular vehicle at the rate of from 1 to 200 mg/ml.

A particularly useful form for administering the compounds of this invention to humans by the oral route is a one-piece gelatin capsule containing 35 mg. of, for example, 1-(6-methoxy-2-benzothiazolyl)-3-phenyl urea mixed with .292 mg. of butylated hydroxy toluene, 29.167 mg. of glycerin and 598.541 of polyethylene glycol 400 to form an encapsulatable paste. 70 mg. gelseals are similarly constituted. Another formulation suitable for oral administration is a telescoping gelatin capsule containing, for example, 50 mg. of 1-(6-methoxy-2-benzothiazolyl)-3-phenyl urea, 2.5 mg. of polyoxyethylene sorbitan monooleate and 47.5 mgs. of microcrystalline cellulose admixed with sodium carboxymethyl cellulose, or 100 or 250 mg. multiples thereof.

In addition to demonstrations of immuno-alterant activity by this group of compounds when administered by the intraperitoneal route, activity by other administration routes has been shown. Subcutaneous, percutaneous, and oral activity have been achieved as indicated in Table 16 which follows employing representative compounds from the above entitled application. For comparative purposes, data obtained using three known immunosuppressives-azathioprine (Imuran), cyclophosphamide (Cytoxan), and cortisone—are included. Except as indicated, the tests were performed using groups of five 20-gram male Swiss mice injected with $5 \times 10^7$ sheep red blood cells intravenously for each drug level. Ten (daily) administrations of drug were made commencing three days prior to red blood cell injection. On the day following the final treatment (7 days after red blood cell injection) the animals were bled by cardiac puncture, the sera from each five-mouse-group were pooled, and antibody titers of these serum pools and corresponding serum pools from control (untreated) mouse groups were determined. The results are expressed as the minimum drug dose effecting 75 percent reduction of control antibody titer:

TABLE 16

| Compound | Lowest Dose Producing 75% Immunosuppression | | |
|---|---|---|---|
| | Subcutaneous (Mg/Kg × 10) | Percutaneous (Mg/Kg × 10) | Oral (Mg/Kg × 10) |
| 1-(2-benzimidazolyl)-3-phenyl urea | 31.5* | | |
| 1-(4,5,6,7-tetrahydro-2-benzothiazolyl)-3-phenyl urea | 12.5 | 3.1 | 25–100 |
| 1-(2-benzothiazolyl)-3-phenyl urea | 1.0 | 6.2–12.5 | 25 |
| 1-(6-methoxy-2-benzothiazolyl)-3-phenyl urea | 0.8–1.6 | 12.5 | 12.5–25 |
| Azathioprine | 50–100 | 100 | 50 |
| Cyclophosphamide | | 25 | 25 |
| Cortisone | 25 | 50 | 200–400** |

*Therapy consisted of seven doses, given once daily, commencing the day of antigen administration
**Antigen given intraperitoneally In order to determine if the compounds disclosed herein had immunoalterant activity in a primate species, representative numbers of the series were tested in marmosets. 1-(2-Fluorophenyl)-3-(6-methoxy-2-benzothiazolyl) urea was injected in 25 mg/kg doses daily for three days into five marmosets. A similar group of five untreated marmosets was reserved as a control series. On the day following the third treatment, all animals received intraperitoneal injections of antigen ($1 \times 10^9$ sheep red blood cells). On the 7th day following antigen injection, serum levels of antibody to the sheep red blood cell antigen were determined. Of the five control animals, four gave antibody responses (titers from 1–10 to 1–80); whereas, only one of the treated animals showed detectable antibody (titer of 1–10).

Oral immunoregulating activity of 1-(6-methoxy-2-benzothiazolyl)-3-phenyl urea was demonstrated in similar groups of marmosets. The animals in the treated group received 10 daily 100 mg/kg doses of the drug by oral gavage. On the 4th treatment day, these animals and a similar group of controls were given intraperitoneal injections of $1 \times 10^9$ sheep red blood cells. On the 12th day following antigen injection, serum levels of antibody were determined. In the control group, four out of five animals had demonstrable antibody, whereas, none of the treated marmosets showed a detectable response. The above data are summarized in Table 17 below.

TABLE 17

| Marmoset Number | Antibody Titer (reciprocal) Day +12* | Weight Change (%) | |
|---|---|---|---|
| | | Day −7 to +6* | Day +6 to +19* |
| Control group: | | | |
| 10 | 320 | −9.6 | +3.6 |
| 17 | 40 | +2.3 | +1.6 |
| 22 | <5 | +1.8 | +4.5 |

TABLE 17-continued

| Marmoset Number | Antibody Titer (reciprocal) Day +12* | Weight Change (%) | |
|---|---|---|---|
| | | Day −7 to +6* | Day +6 to +19* |
| 216 | 160 | −4.9 | −1.6 |
| 227 | 80 | 0.0 | +3.1 |
| Treated group: | | | |
| 5 | <5 | −18.8 | −6.8 |
| 25 | <5 | −6.2 | +9.1 |
| 207 | <5 | −21.4 | +6.0 |
| 225 | <5 | −5.7 | +5.7 |
| 226 | <5 | −8.2 | +6.0 |

*Notation: Day 0 = day of antigen injection, Day −1 = day previous, Day +1 = day following, etc.

While weight loss on the 6th day following antigen was more common in the treated group, by the 19th day, four of the five animals were gaining weight. The weight changes may reflect the arbitrarily selected high drug dose level. The relative scarcity of these animals precluded any elaborate dose-response studies. However, the marked immunoregulating response observed establishes activity in a primate species.

NZB/w mice provide a close model of the human autoimmune disease, lupus erythematosis. These hybrid mice develop antinuclear autoantibody in the early months of life, which antibody becomes deposited in the glomeruli in the form of a complex with the inciting antigen. A fatal glomerulonephritis ensues. A group of these mice had been placed under continuous therapy (via the feed) with 1-(6-methoxy-2-benzothiazolyl)-3-)phenyl urea for 300 days. The mice were divided into three subgroups, 10 mice receiving 75 mg/kg/day of drug, 10 mice receiving 25 mg/kg/day, and 11 mice serving as untreated controls. The death pattern and derivative values (% survivors, mean survival time) as of the 300th day of therapy are shown in Table 18 below.

TABLE 18

| Treatment (Mg/Kg/Day) | Day of Death | Percent Survivors | MST (Days) |
|---|---|---|---|
| 75 | 180,281 | 80 | 286 |
| 25 | 37,68,113,124 | 60 | 214 |
| 0 | 58,63,71,141,181,214 | 45 | 202 |

A dose-related effect of the drug on survival parameters has been observed continuously since deaths began to occur. While the determinations are incomplete (the survivors will eventually be electively sacrificed and pathological examinations for glomerular and other effects on all animals will be made; also antinuclear antibody determinations will be made on periodically collected sera), the results following 300 days of therapy indicate therapeutic immunoregulating effect without gross toxicity. In view of the close parallel of this murine model to the human counterpart, this would appear of significance in terms of long-term human therapy.

Compounds disclosed herein have shown activity in suppressing the rejection of mouse skin grafts. The Bailey and Usama mouse-tail skin procedure (Transplantation Bulletin 7:424–425, 1960) was utilized. Albino tail skin segments (AKR strain) were grafted onto the tails of groups of ten agouti recipient mice (C3H strain). Results achieved with two therapy regimens employing 1-(6-methoxy-2-benzothiazolyl)-3-phenyl urea were as follows:

TABLE 19

| Dosage* | Route- | Allograft Survival (Days ± S.E.) | |
|---|---|---|---|
| (Mg/Kg/2 Days) | Vehicle | Treated | Control |
| 50 | Subcutaneous-POT** | 27.7 ± 1.0 | 19.6 ± 1.3 |
| 50 | Oral - POT | 25.2 ± 2.0 | 19.6 ± 1.3 |

*Treatment was commenced 3 days prior to grafting and continued every 2nd day until slough.
**50% polyethylene glycol, 40% corn oil, 10% Tween 80

Such results have significance for therapy of human tissue transplant rejection and therapy of autoimmune diseases of the cellular-immune type.

The graft versus host reaction has been utilized as a model of the cellular immune reaction in order to demonstrate suppression of this component of the immune response. In this determination, parenteral (C57BL) mouse spleen cells are injected into mice of an $F_1$ hybrid strain (C57BL×C3H). The recipient mice do not reject the injected spleen cells, due to common parentage. The injected cells, however, mount a reaction to the recipient's tissues due to the foreign C3H-derived antigens. As a consequence, the recipient's spleen becomes enlarged. Immunosuppressive therapy prevents or reduces this enlargement. Thus, spleen weights provide a measure of the GVH reaction and its reduction under immunosuppression.

Treated and GVH control animals receive an intraperitoneal injection of $1.2 \times 10^9$ splenic lymphocytes from the C57 donors. Spleens are weighed ten days later. Spleen weights derived from groups of recipient mice receiving genetically homologous, i.e., syngeneic cells (C57BL×C3H) provide normal control values for calculating percent inhibition in drug-treated groups. For example, mice given 13 daily topical doses of 1-(4,5,6,7-tetra-hydro-2-benzothiazolyl)-3-phenyl urea show a 62% reduction in GVH reaction relative to controls, as set forth in Table 20.

TABLE 20

| Treatment | Mg Spleen/g Body Weight ± S.E.** | Percent Inhibition*** |
|---|---|---|
| 100 mg/kg × 13* | 7.42 ± 0.63 | 62 |
| None (GVH Control) | 11.03 ± 0.35 | 0 |
| None (Syn. Control) | 5.20 ± 0.37 | 100 |

*Daily topical treatments commencing 3 days prior to cell injection. Controls received vehicle alone.
**Mean values from groups of 5 mice.
***$\frac{\text{GVH-Treated}}{\text{GVH-Syn.}} \times 100$ = Percent inhibition Using this procedure, three compounds from the above useful in the processes of this invention have been compared with several reference immunosuppressive drugs. Treatment levels defining the 50 percent inhibitory dose have been determined. The data are presented in Table 20 below.

TABLE 21

| Compound | Dose (Mg/Kg × 13) | Route | Percent GVH Inhibition |
|---|---|---|---|
| 1-(4,5,6,7-tetrahydro-2-benzothiazolyl)-3-phenyl urea | 100 | oral | 54 |
| | 50 | oral | 41 |
| 1(-2-benzothiazolyl)-3-phenyl urea | 3.12 | oral | 64 |
| | 1.6 | oral | 46 |
| | 1.6 | s.c. | 54 |
| | 0.8 | s.c. | 29 |
| 1-(6-methoxy-2-benzothiazolyl)-3-phenyl urea | 2 | s.c. | 58 |
| | 1 | s.c. | 22 |
| Cytoxan | 12.5 | s.c. | 53 |
| | 6.25 | s.c. | 32 |
| Imuran | 10 | s.c. | 61 |
| | 5 | s.c. | 43 |
| Cortisone | 3.12 | s.c. | 82 |
| | 1.56 | s.c. | 48 |

Varying degrees of suppression of this aspect of the immune response have been detected among compounds of the present novel class. As indicated above, activity approximating or exceeding that of several currently employed immunosuppressives has been demonstrated. These observations would have relevance for therapy of autoimmune diseases of the cellular immune type and for therapy of tissue transplant rejection.

The heterocyclic ureas useful in altering the immune response according to the processes of this invention, as can be seen, differ from hitherto known immune regulants and immunosuppressants in the mechanism of their action on the mammalium host. They do not act by directly antagonizing the action of histamine as do the anti-histamine drugs. On the other hand, they do not depress bone-marrow function as do the antineoplastic drugs frequently used in connection with tissue transplants. The heterocyclic ureas more closely resemble the corticoids in their effects on the immune response, but even here there is a fundamental difference in that the corticoids deplete lymoid tissue and the heterocyclic ureas do not. Thus, it is apparent that these agents function through a mechanism which neither depletes normal lymphoid mass nor depresses bone marrow, thus avoiding the major drawbacks of the currently used immunosuppressive drugs-the corticosteroids and antineoplastic drugs.

One of the compounds of this invention has been tested for its mutagenic potential because of the fact that several useful immunosuppressants are known to have carcinogenic properties.

The in vivo and in vitro mutagenic potential of 1-(6-methoxy-2-benzothiazolyl)-3-phenyl-urea was negative when tested versus the twelve histidine-auxotrophs of Salmonella typhimurium at a level of 300 mg/kg in vivo and 750 mcg/ml in vitro. Imuran and Cytoxan, compounds with immunosuppressive activity; Streptozotacin, N-nitrosodimethylamine (DMNA) and trimethylenemelamine (TEM) known mutagens and/or carcinogens; and Acetylsalicylic Acid (ASA) were used as control compounds.

The following organisms were employed:

| G46 | his-, missense |
|---|---|
| TA1530 | G46 containing gal-bio-urv B deletion |

| | |
|---|---|
| TA1535 | G46 containing gal-bio-urv B and LPS deletion |
| C207 | his- (−) frameshift |
| TA1531 | C207 containing gal-bio-urv B deletion |
| TA1536 | C207 containing gal-bio-urv B and LPS deletion |
| C3076 | his- (+) fameshift |
| TA1531 | C3076 containing gal-bio-urv B deletion |
| TA1537 | C3076 containing gal-bio-urv B and LPS deletion |
| D3056 | his- (+) frameshift |
| TA1534 | D3056 containing gal-bio-urv B deletion |
| TA1538 | D3056 containing gal-bio-urv B and LPS deletion |

These organisms are fully described by Ames, Bruce N.; Frank D. Lee; and William Durston, *Proc. Nat. Acad. Sci.*, Vol. 70, 782–786 (1973)

The following media were employed:

A. Cultures were maintained in tryptone-yeast broth (1.0% tryptone, 0.5% yeast extract).

B. Spizizen's minimal media with trace amounts of biotin and histidine was the base media used. Selection of histidine− and histidine+ organisms was accomplished by using the following top agars.

1. histidine+: 1.5% agar with 0.5% NaCl
2. histidine−: 1.5% agar with 0.5% NaCl and excess histidine (40 mcg/ml)

Cox white Swiss male mice 25–30 grams were used in all in vivo tests.

The following test methods were followed:

I. Qualitative In Vitro Prescreen

Filter paper discs ¼" were impregnated with 200 mcg of test compound using either $H_2O$ or DMSO as solvent. The discs were placed on Petri dishes containing minimal media which had been individually seeded with one of the twelve tester strains. The histidine− tested strains do not grow. If the test compound causes a histidine-bacterium to revert to histidine+, that bacterium is able to produce a colony. A uniform circle of colonies appear around the pad when a compound with mutagenic potential is present. The test compound forms a concentration gradient as it diffuses from the pad. Occasionally, there is a clear ring in close proximity to the pad surrounded by a uniform circle of revertant colonies which indicates a lethal mutation at high concentration of compound and nonlethal mutation at lesser concentration. A single pad thus allows one to test a compound over a wide range of concentrations. Histidine+ colonies were developed enough to read after 48 hr. incubation at 37° C. The plates were read as follows:

A. Background zone, if present, is measured in millimeters, if not, a negative is recorded (−).

B. Mutant zone is measured in millimiters, if present; if not, a negative (−) is recorded.

C. The mutation frequency can be estimated from density of mutant colonies as follows:
1. Low frequency—few colonies
2. Moderate frequency—many colonies
3. High frequency—dense ring of colonies
4. No colonies recorded (−)

II. Quantitative In Vitro Testing

Compounds found active in the qualitative test were further tested. The culture to be tested was grown to stationary phase in tryptone yeast broth and then diluted to a viable count of about $9 \times 10^7$ organisms per milliliter.

Eleven $\log_4$ dilutions of the test compound were made covering a range that would allow survival of nonlethal mutants. The dilutions were made in Spizizen's minimal media with minute amounts of histidine and biotin (20 nM) each in $18 \times 120$ ml. tubes. Each tube contained 3 ml. after dilution. Replicate 1 ml. aliquots of test organism were added to each tube including six "0" drug tubes. Final drug concentrations were calculated from 4-ml. volumes (3 ml. drug dilution +1 ml. test organism). Two of the "0" drug tubes were immediately plated at 10° dilution in minimal medium and $10^{-5}$, $10^{-6}$, $10^{-7}$ dilutions in medium containing excess histidine (40 mcg/ml.) Spontaneous revertants (histidine+) were detected in the 10° dilution. Mutable population (histidine−) were detected in the $10^{-5}$, $10^{-6}$, and $10^{-7}$ dilutions. All remaining dilutions were incubated in a Dubonoff shaker at 37° C. for 4 hr., then iced at 4° C. A 1-ml. aliquot from all incubated tubes were plated at 10° dilution on minimal media to determine if the compound induced revertants (histidine+). A 1-ml. aliquot from each "0" control was also plated at $10^{-6}$, $10^{-7}$, and $10^{-8}$ dilutions in media with excess histidine to detect growth of mutable population (histidine−); normally there are 3–4 generations of the mutable population. All minimal media plates were counted. A dose response increase in revertants above spontaneous background indicated mutagenic potential of a test compound. If gross inhibition was noted in any treated tube, platings were made to determine lethality to the mutable population (histidine−). Lethality has occurred to both populations, histidine+ and histidine−, at the same compound levels in all drugs tested to date.

III. Host Mediated Assay (In Vivo)

A. Drug Administration: Appropriate solvents were used where applicable with a solvent control run within each test. The compounds to be tested were given either subcutaneously along the backbone of the mouse (0.1 ml.) or by oral gavage (0.5 ml.) B. Inoculation Technique: The histidine− cultures G46, C209, C3076, and D3056 used as the TA15 series have lost pathogenicity to mice because of absence or decrease in the lipopolysaccharide coat. The organisms were grown to stationary phase, then diluted with normal saline to give an inoculum near $1 \times 10^8$ organisms per milliliter. The abdominal area of the drug-treated mouse was swabbed with alcohol and two milliliters of bacterial culture were injected into the abdominal cavity of the mouse. The mice were returned to their cages for 3–4 hours.

C. Autopsy and Recovery: The mice were sacrificed individually by cervical dislocation prior to each autopsy. The abdominal areas were soaked with ethanol. The peritoneum was bared and 2.5 ml. of sterile normal saline was injected into the peritoneal cavity using a sterile (3-ml. plastic syringe with a 20-gauge needle. After insertion, the needle is turned bevel up and the saline was expelled into the cavity; while the needle remains through the peritoneum, keeping the point of the needle in sight pressed against the peritoneal wall, the abdomen of the mouse was massaged to mix contents. The saline wash was removed from the abdominal cavity back into the syringe. The needle was removed and the contents expelled into an appropriately marked tube and iced 4° C.

D. Dilution and Plating: One-ml. samples were plated at 10° dilution on all mice to determine revertants (histidine+).

A one-milliliter sample from the untreated dilutions from control animals is plated $10^{-6}$, $10^{-7}$, and $10^{-8}$ dilutions with excess histidine to determine mutable population (histidine−).

E. Scoring

1. Mutation frequency = $\frac{\text{histidine} + /\text{ml.}}{\text{histidine} - /\text{ml.}}$ 2. $MFT/MFC = \frac{\text{mutation frequency test}}{\text{mutation frequency control}}$ a. MFT/MFC of control = 1

3. $MT/MC = \frac{\text{histidine} + /\text{ml. test}}{\text{histidine} + /\text{ml. control}}$ MT/MC of control = 1

F. Organism Control

Contamination: There is a chance that the mouse gut can be nicked during manipulations. When this happens, colonies will appear on the minimal plates which could be misinterpreted and a drug called falsely, a mutagen. A suspect culture is plated on MacConkey's agar, if coliform colonies are present, the culture is discarded; if there is no growth, the culture is also discarded.

G. Mutagen Control

The histidine-auxotrophs do have a definite mutagenic spectrum and the input and output are checked for compliance. A host-mediated assay is described by Legator, M. S. and Malling, H. V.: *The Host Mediated Assay. A Practical Procedure for Evaluating Chemical Mutagens.* (*Chemical Mutagens. Principles and Methods for Their Detection* Hollaender, A., ed. Plenum Press, 2; 569–589, (1971), New York.)

Results: No activity was noted by any of the compounds in the C3076 frameshift system; therefore, Table 22 contains a summary of in vitro and in vivo data using the G46 missense histidine-auxotroph as the indicator organism. The results are recorded as mutants test/mutants control.

Cytoxan was toxic to the animals at high levels. DMNA is a compound requiring host-mediation to demonstrate mutagenic potential. 1-(6-methoxy-2-benzothiazolyl)-3-phenylurea appears to be non-mutagenic when tested for point mutations using histidine— auxotrophs of *Salmonella typhimurium* as indicators.

74,290 (1973) reported a 58 percent increase in neoplasms in azathioprine-treated mice (0 percent incidence in the control series). Walker and Bole reported in *J. Lab. Clin. Med.*, 82,619 (1972) a 100 percent incidence of neoplasms in their series of cyclophsphamide-treated mice compared with 5 percent incidence in the control series. It is apparent that the mechanism of action of the immune regulants of this invention does not parallel their carcinogenic potential as it does in the known anti-neoplastic agents presently used as immune suppressants.

We claim:

1. The method for regulating the immune response which comprises administering to a mammal suffering from an immune reaction a dose of from 0.1 to 500 mg/kg of mammalian body weight of a compound of the formula:

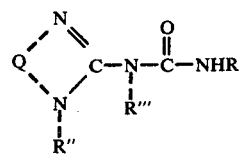

wherein R is α-naphthyl, phenyl or substituted phenyl or substituted phenyl wherein said substituents can be one or two members of the group consisting of halo, $C_1$–$C_3$ alkoxy, $C_1$–$C_3$ alkyl or $CF_3$, R″ and R‴ are independently H or $CH_3$ and Q is

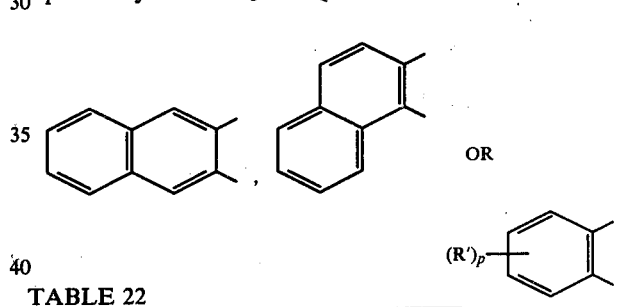

wherein R′ in each of its "p" occurrences independently represents halo, $CF_3$, carb-$C_1$–$C_3$-alkoxy, nitro, $C_1$–$C_3$ alkyl or $C_1$–$C_3$ alkoxy and p is 0–2.

2. A method according to claim 1 in which N-4(7)-nitro-2-benzimidazolyl-N′-(2-fluorophenyl)urea is administered.

3. A pharmaceutical formulation in dosage unit form comprising an effective amount to regulate the immune response of N-4(7)-nitro-2-benzimidazolyl-N-(2-fluorophenyl) urea plus a pharmaceutical carrier.

TABLE 22

| | IN VIVO | | | | | QUALITATIVE | | QUANTITATIVE | |
|---|---|---|---|---|---|---|---|---|---|
| (MG/KG) | 300 | 30 | 3 | .3 | .03 0 | ACTIV-ITY | FREQ | MT/MC | MCG/ML |
| STREPTOZOTOCIN | ND | 444[4] | 2782 | 278 | 3.35 1.0 | P | HIGH | 6750 | .11 |
| DMNA[1] | 620 | 43.6 | 1.16 | ND | ND 1.0 | N | — | .33 | 750 |
| TEM | 13 | 27 | 13 | 3.2 | ND 1.0 | P | MEDIUM | 24 | 180 |
| ASA[2] | 1.06 | 1.11 | ND | ND | ND 1.0 | N | — | .58 | 750 |
| IMURAN[3] | 5.93 | 1.96 | 1.03 | ND | ND 1.0 | N | — | ND | ND |
| CYTOXAN | TOXIC | 1.30 | 1.16 | ND | ND 1.0 | N | — | ND | ND |
| 53616 | 1.2 | .95 | .95 | 1.25 | ND 1.0 | N | — | .90 | 750 |

ND = NOT DONE
P = POSITIVE
N = NEGATIVE
[1]REQUIRES HOST MEDIATION
[2]ORAL GAVAGE, ALL OTHER COMPOUNDS GIVEN S.C.
[3]IMURAN SHOWS POSSIBLE MUTAGENIC POTENTIAL IN THE HOST-MEDIATED SYSTEM AT HIGH LEVELS.
[4]MT/MC OF 3 WOULD INDICATE MUTAGENIC POTENTIAL.

1-(6-methoxy-2-benzothiazolyl)-3-phenyl urea as previously stated was able to prolong the life of female NZBxW mice, females, of which strain of mice customarily developed a fatal autoimmune glomerulonephritis. Because of the consequent increase in life span of the treated mice, there is also a small increase in the incidence of neoplasms observed in the treated animals—12.5 percent against a 4 percent increase in a control group. By contrast, there is a marked augmentation in the incidence of neoplasms in groups of female NZBxW mice receiving therapeutically effective levels of the autoimmune agents--azathioprine and cyclophosphamide. Casey, writing in *New Zealand Medical Journal,*